United States Patent
Hyodo et al.

(10) Patent No.: US 8,552,717 B2
(45) Date of Patent: Oct. 8, 2013

(54) EDDY CURRENT TESTING METHOD AND EDDY CURRENT TESTING APPARATUS

(75) Inventors: Shigetoshi Hyodo, Osaka (JP); Yoshiyuki Nakao, Osaka (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 582 days.

(21) Appl. No.: 12/531,840

(22) PCT Filed: Mar. 17, 2008

(86) PCT No.: PCT/JP2008/054855
§ 371 (c)(1),
(2), (4) Date: Feb. 12, 2010

(87) PCT Pub. No.: WO2008/123035
PCT Pub. Date: Oct. 16, 2008

(65) Prior Publication Data
US 2010/0148767 A1      Jun. 17, 2010

(30) Foreign Application Priority Data

Mar. 26, 2007  (JP) ................................. 2007-078319

(51) Int. Cl.
*G01N 27/82*        (2006.01)
(52) U.S. Cl.
USPC ........... 324/237; 324/238; 324/240; 324/216; 324/718; 324/456
(58) Field of Classification Search
USPC .................. 324/237, 238, 456, 216, 240, 718
See application file for complete search history.

(56) References Cited

U.S. PATENT DOCUMENTS

| | | | | |
|---|---|---|---|---|
| 6,014,024 A | * | 1/2000 | Hockey et al. | 324/240 |
| 6,822,443 B1 | * | 11/2004 | Dogaru | 324/235 |
| 2002/0153883 A1 | * | 10/2002 | Hur et al. | 324/220 |

FOREIGN PATENT DOCUMENTS

| | | |
|---|---|---|
| JP | 53-28467 | 3/1978 |
| JP | 58-68662 | 4/1983 |
| JP | 61-277052 | 12/1986 |

OTHER PUBLICATIONS

English translation of International Search Report as issued in PCT/J2008/054955 on Jun. 17, 2008.

*Primary Examiner* — Arleen M Vazquez
*Assistant Examiner* — Alesa Allgood
(74) *Attorney, Agent, or Firm* — Marshall, Gerstein & Borun LLP (57) ABSTRACT

It is an object of the present invention to provide an eddy current testing apparatus capable of accurately detecting any flaws occurring in a columnar or cylindrical subject to be tested regardless of their extending directions, with the use of the same probe coil.
The eddy current testing apparatus 100 according to the present invention comprises a spinning plate 1 and a probe coil 2 disposed on the spinning plate 1. The probe coil is a probe coil capable of obtaining a differential output about a scanning direction of a detection signal which corresponds to a detected eddy current induced in the subject to be tested. The spinning plate is disposed in such a position that a spinning center RC of the spinning plate faces with an axial center PC of the subject to be tested. A distance R between the spinning center of the spinning plate and a center of the probe coil is set so that a difference between a maximum amplitude of a differential output at an axially extending artificial flaw provided in the subject to be tested and a maximum amplitude of a differential output at a circumferentially extending artificial flaw provided in the subject to be tested falls within a predetermined range.

2 Claims, 4 Drawing Sheets

EDDY CURRENT TESTING METHOD AND EDDY CURRENT TESTING APPARATUS

FIELD OF THE INVENTION

The present invention relates to an eddy current testing method and an eddy current testing apparatus for detecting a flaw occurring in a columnar or cylindrical subject to be tested such as a steel pipe or tube or a steel bar. In particular, the present invention relates to an eddy current testing method and an eddy current testing apparatus capable of accurately detecting any flaws occurring in a columnar or cylindrical subject to be tested regardless of their extending directions, with the use of the same probe coil. Hereinafter, "pipe or tube" is referred to as "pipe" when deemed appropriate.

DESCRIPTION OF THE RELATED ART

Various flaws occur in a steel pipe or a steel bar, and a non-destructive testing method such as an eddy current testing method is conventionally used for detecting these flaws. As for a flaw originating from a material, the flaw generally extends axially because it is extended in the axial direction of the steel pipe or the steel bar by rolling. On the other hand, as for a flaw arising during a rolling process, the flaw extends in the direction of stress or in the direction resulting from a metal flaw at the time of rolling. Thus flaws extending in various directions occur in a steel pipe or a steel bar, so that it is requested to accurately detect any flaws regardless of their extending directions.

Conventionally, as an eddy current testing method for detecting flaws extending in various directions, for example, the method disclosed in Japanese Unexamined Patent Publication No. 2-173560 is proposed. Concretely, Japanese Unexamined Patent Publication No. 2-173560 discloses an eddy current testing method for detecting a flaw while moving a subject to be tested, relative to a sensor coil that forms a vertical magnetic field with respect to a face of the subject to be tested, wherein the sensor coil is disposed on a spinning plate, and the spinning plate is spun to make the sensor coil scan at an angle of approximately 45 degrees with respect to the moving direction of the above relative movement (See, for example, columns of claims of Japanese Unexamined Patent Publication No. 2-173560).

According to the method of Japanese Unexamined Patent Publication No. 2-173560, since the sensor coil is caused to scan at an angle of 45 degrees with respect to the moving direction of the relative movement (axial direction of the subject to be tested), it can be said that an ability to detect a flaw extending in the direction orthogonal to the scanning direction (direction at an angle of 135 degrees with respect to the axial direction of the subject to be tested) is excellent. However, as for a flaw extending in the axial direction (hereinafter, referred to as "axial flaw"), and a flaw extending in the circumferential direction (hereinafter, referred to as "circumferential flaw"), both of these may be passed over because of deterioration in flaw detection sensitivity (maximum amplitude of an output signal of a sensor coil at a flaw).

As described above, the conventional eddy current testing method has a problem that an accurate detection at the same time is not achieved both for an axial flaw and a circumferential flaw, and for flaws extending in intermediate directions using the same sensor coil (probe coil).

SUMMARY OF THE INVENTION

The present invention was devised to solve the above problems of the conventional arts, and it is an object of the present invention to provide an eddy current testing method and an eddy current testing apparatus capable of accurately detecting any flaws occurring in a columnar or cylindrical subject to be tested regardless of their extending directions, with the use of the same probe coil.

In order to solve the above problems, inventors of the present invention made diligent efforts and obtained the following findings (1) to (3).

(1) By using, as a probe coil conducting spinning scanning, a probe coil by which a differential output about a scanning direction of a detection signal which corresponds to a detected eddy current induced in a subject to be tested is obtained, it is possible to suppress an amplitude of a noise signal resulting from a liftoff variation between the probe coil and the subject to be tested.

(2) By setting a radius of spinning in spinning scanning of the probe coil equal to or smaller than an outer radius of the subject to be tested and making the spinning center of the probe coil opposite to the axial center of the subject to be tested, it is possible to make the probe coil scan in the direction orthogonal to the direction in which the flaw extends for any flaws occurring in the subject to be tested regardless of their extending directions. As a result, it is possible to increase the flaw detection sensitivity (maximum amplitude of differential output) compared to the case where the probe coil is not made to scan in the direction orthogonal to the direction in which the flaw extends.

(3) However, when the radius of spinning is set too large, a liftoff between the probe coil and the subject to be tested largely varies in one spin, so that a difference in detection sensitivity of flaws extending in various directions increases. Concretely, since the liftoff is a minimum in the condition that the probe coil is made to scan in the direction orthogonal to an axial flaw, the detection sensitivity is the highest for the axial flaw among flaws extending in various directions. On the other hand, since the liftoff is a maximum in the condition that the probe coil is made to scan in the direction orthogonal to a circumferential flaw, the detection sensitivity is the lowest for the circumferential flaw among flaws extending in various directions. The larger the radius of spinning of the probe coil, the larger the difference in detection sensitivity between the axial flaw and the circumferential flaw becomes because the larger the difference in the liftoff becomes. Therefore, in order to accurately detect both an axial flaw and a circumferential flaw, and further any flaws extending in intermediate directions thereof, it is important to set the radius of spinning so that the difference in detection sensitivity between the axial flaw and the circumferential flaw falls within an allowable range.

The present invention was accomplished based on the above findings found by the present inventors. To be more specific, the present invention provides an eddy current testing method for detecting a flaw occurring in a columnar or cylindrical subject to be tested by conducting spinning scanning of a probe coil disposed to be opposite to the subject to be tested, relative to the subject to be tested, wherein as the probe coil, a probe coil capable of obtaining a differential output about a scanning direction of a detection signal which corresponds to a detected eddy current induced in the subject to be tested is used, a spinning center of the probe coil is disposed to face with an axial center of the subject to be tested, and a distance between the spinning center of the probe coil and a center of the probe coil is set so that a difference between a maximum amplitude of a differential output at an axially extending artificial flaw provided in the subject to be tested and a maximum amplitude of a differential output at a circumferentially extending artificial flaw provided in the subject to be tested falls within a predetermined range.

The term "probe coil" used herein includes both a self-induction type coil in which a detection coil also functions as an excitation coil that causes an AC magnetic field to act on a subject to be tested, and a mutual induction type coil in which a detection coil and an excitation coil are implemented by separate members. As a "probe coil by which a differential output about a scanning direction of a detection signal which corresponds to a detected eddy current induced in a subject to be tested is obtained" in the present invention, a so-called self comparing type probe coil can be exemplified that has a pair of detection coils disposed in parallel to each other along the scanning direction of the probe coil, and is configured to output a difference in detection signal (differential output) between the detection coils disposed to face with a subject to be tested. It is not necessarily required to make the direction in which the pair of detection coils are disposed in parallel with each other into perfect coincidence with the scanning direction of the probe coil, and the pair of detection coils may be disposed in parallel with each other, in the direction inclined from the scanning direction of the probe coil as far as a differential output can be obtained at an artificial flaw extending in the direction orthogonal to the scanning direction of the probe coil (differential output is distinguishable from noise signals at artificial flaw). It is also possible to use a probe coil which is a so-called uniform eddy current coil, having a circular excitation coil, and a rectangular detection coil disposed in the excitation coil and configured to detect a magnetic field in the scanning direction of the probe coil (lead wire is wound about the scanning direction). It is not necessarily required to make the direction of axial center of the rectangular detection coil (magnetic field detecting direction) into perfect coincidence with the scanning direction of the probe coil and the rectangular detection coil may be disposed while its axial center is inclined from the scanning direction of the probe coil as far as a differential output can be obtained at an artificial flaw extending in the direction orthogonal to the scanning direction of the probe coil (differential output is distinguishable from noise signals at artificial flaw). Further, the wordings "spinning center of the probe coil is made to face with the axial center of the subject to be tested" used herein means the condition that a straight line passing the spinning center of the probe coil crosses with the axial center of the subject to be tested at right angles.

In order to solve the above problems, the present invention also provides an eddy current testing apparatus having a spinning plate and a probe coil disposed on the spinning plate, for detecting a flaw occurring in a columnar or cylindrical subject to be tested by spinning the spinning plate disposed to be opposite to the subject to be tested, relative to the subject to be tested, thereby conducing spinning scanning of the probe coil, wherein the probe coil is a probe coil capable of obtaining a differential output about a scanning direction of a detection signal which corresponds to a detected eddy current induced in the subject to be tested, the spinning plate is disposed in such a position that a spinning center of the spinning plate faces with an axial center of the subject to be tested, and a distance between the spinning center of the spinning plate and a center of the probe coil is set so that a difference between a maximum amplitude of a differential output at an axially extending artificial flaw provided in the subject to be tested and a maximum amplitude of a differential output at a circumferentially extending artificial flaw provided in the subject to be tested falls within a predetermined range.

According to the present invention, since the probe coil can be made to scan in the direction orthogonal to the direction in which a flaw extends, for any flaws occurring in a columnar or cylindrical subject to be tested regardless of their extending directions, it is possible to improve the flaw detection sensitivity (maximum amplitude of differential output). Further, since the distance between the spinning center of the probe coil and the center of the probe coil is set so that a difference in detection sensitivity (difference in maximum amplitude of differential output) between an axial flaw (artificial flaw extending in the axial direction) and a circumferential flaw (artificial flaw extending in the circumferential direction), which is a maximum difference, falls within a predetermined allowable range, it is possible to make a difference in detection sensitivity fall within the allowable range for any flaws regardless of their extending directions. Therefore, according to the present invention, it is possible to accurately detect any flaws occurring in a subject to be tested regardless of their extending directions, with the use of the same probe coil.

BRIEF DESCRIPTION OF THE DRAWINGS

FIGS. 1A and 1B are views showing schematic configuration of an eddy current testing apparatus according to one embodiment of the present invention, in which

FIGS. 2A and 2B are views for explaining the condition in which the probe coil shown in FIGS. 1A and 1B is spun for scanning, in which

FIGS. 6A and 6B are explanatory views showing an outline of a test executed in setting a radius of spinning of a probe coil constituting an eddy current testing apparatus according to the present invention, in which

DETAILED DESCRIPTION OF THE PREFERRED EMBODIMENTS

In the following, one embodiment of the present invention will be explained while taking the case where a subject to be tested is a steel pipe as an example, with reference to attached drawings as appropriate.

<Makeup of Eddy Current Testing Apparatus>

Figure 1A:
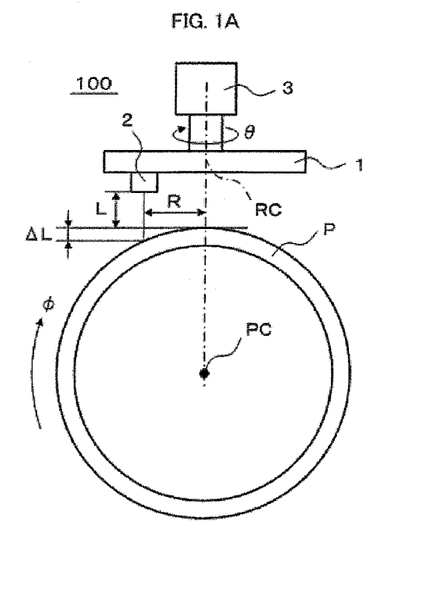
FIG. 1A is a front view.
Figure 1B:
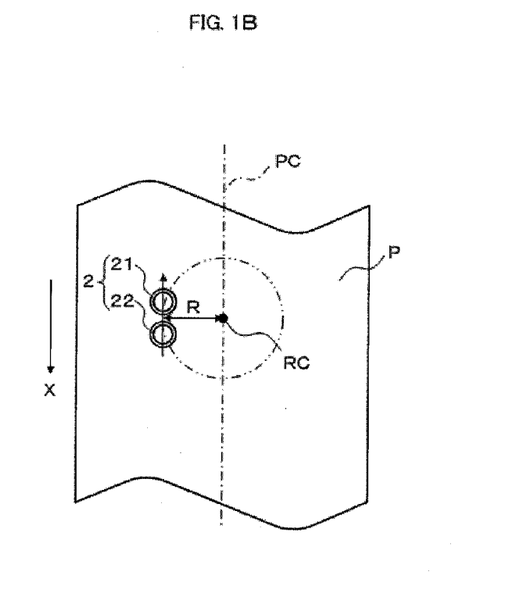
FIG. 1B is a plane view of a probe coil shown in FIG. 1A.
Figure 2A:
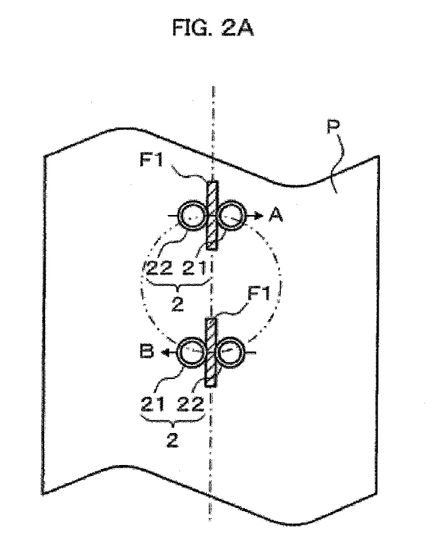
FIG. 2A shows the condition that the probe coil is made to scan in the direction orthogonal to an axial flaw.
Figure 2B:
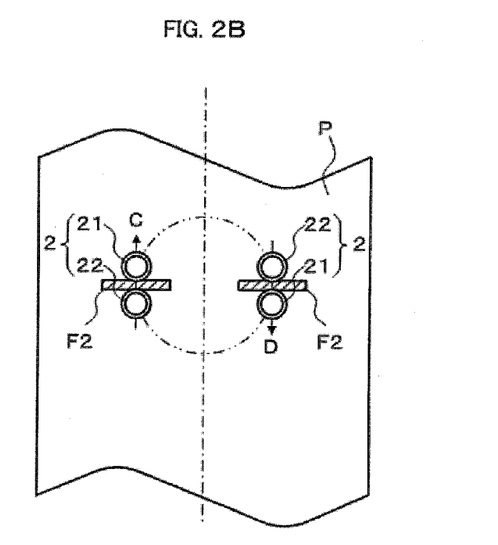
FIG. 2B shows the condition that the probe coil is made to scan in the direction orthogonal to a circumferential flaw.

FIGS. 1A and 1B are views showing schematic configuration of an eddy current testing apparatus according to one embodiment of the present invention, in which FIG. 1A is a front view, and FIG. 1B is a plane view of a probe coil shown in FIG. 1A. FIGS. 2A and 2B are views for explaining the condition in which the probe coil shown in FIGS. 1A and 1B is spun for scanning, in which FIG. 2A shows the condition that the probe coil is made to scan in the direction orthogonal to an axial flaw, and FIG. 2B shows the condition that the probe coil is made to scan in the direction orthogonal to a circumferential flaw. As shown in FIGS. 1A and 1B, an eddy current testing apparatus 100 according to the present embodiment has a spinning plate 1 and a probe coil 2 placed on the spinning plate 1, and detects a flaw occurring in a steel pipe P by spinning scanning of the probe coil 2 by spinning the spinning plate 1 disposed to be opposite to the steel pipe P, relative to the steel pipe P (spinning in the direction of arrow θ shown in FIG. 1A). The spinning plate 1 is spun by a spinning driving source 3 such as a motor. To the probe coil 2, a known eddy current testing unit (not illustrated) is connected. This eddy current testing unit is configured to supply the probe coil 2 with an AC current, while detecting a flaw occurring in the steel pipe P based on a differential output outputted from the probe coil 2. The steel pipe P and the spinning plate 1 relatively rotate in the circumferential direction of the steel pipe P (for example, steel pipe P rotates in the direction of arrow φ of FIG. 1A), and relatively move in the axial direction of the steel pipe P (for example, steel pipe P moves in the direction of arrow X in FIG. 1B), whereby the entire outer surface of steel pipe P is tested.

The probe coil 2 is configured to make an AC magnetic field act on the steel pipe P by the AC current supplied by the eddy current testing unit to induce an eddy current, while detecting the eddy current induced in the steel pipe P. And the probe coil 2 is a probe coil by which a differential output about the scanning direction of a detection signal which is the detected eddy current induced in the steel pipe P is obtained. To be more specific, the probe coil 2 according to the present embodiment is a mutual induction type coil in which an excitation coil (not illustrated) for making the AC magnetic field act on the steel pipe P, and a detection coil for detecting an eddy current are implemented by separate members, and functions as a so-called self comparing type coil having a pair of detection coils 21, 22 disposed in parallel with each other along the scanning direction, and configured to output a difference in the detection signal between the detection coils 21, 22 (differential output). The excitation coil of the probe coil 2 makes the AC magnetic field act in the direction perpendicular to the outer surface of the steel pipe P, and the detection coils 21, 22 detect change in the AC magnetic field in the direction perpendicular to the outer surface of the steel pipe P occurring due to the eddy current. These detection coils 21, 22 are disposed in parallel with each other along the scanning direction as described above, and difference in detection signal about the region in the steel pipe P opposing to each of the detection coils 21, 22 (differential output) is outputted from the probe coil 2 by spinning scanning of the probe coil 2 relative to the steel pipe P. Therefore, it is possible to suppress an amplitude of a noise signal resulting from a liftoff variation between the probe coil 2 (in particular, detection coils 21, 22) and the steel pipe P.

The spinning plate 1 is disposed at such a position that a spinning center RC of the spinning plate 1 (corresponding to the spinning center of the probe coil 2) faces with an axial center PC of the steel pipe. That is, a straight line passing the spinning center RC of the spinning plate 1 and the axial center PC of the steel pipe P cross at right angles. And a distance R between the spinning center RC of the spinning plate 1 and the center of the probe coil 2 (corresponding to the radius of spinning of the probe coil 2) is set to be equal to or smaller than the outer radius of the steel pipe P. Accordingly, the probe coil 2 can be made to scan in the direction orthogonal to an extending direction of a flaw, for any flaws occurring in the steel pipe P regardless of their extending directions. As a result, it is possible to improve the flaw detection sensitivity (maximum amplitude of differential output of the probe coil 2) compared with the case where the probe coil 2 is not made to scan in the orthogonal direction.

However, if the radius of spinning R of the probe coil 2 is set to be too large, a liftoff between the probe coil 2 and the steel pipe P largely varies in one spinning, so that a difference in detection sensitivity of flaws extending in various directions (maximum amplitude of differential output) increases. As shown in FIG. 2A, an amplitude of a differential output at an axial flaw F1 occurring in the steel pipe P is a maximum when the probe coil 2 is made to scan in the direction orthogonal to the axial direction of the steel pipe P (direction of arrow A or B shown in FIG. 2A), and at this time, detection sensitivity at the axial flaw F1 is most improved. And the liftoff is a minimum when the probe coil 2 is made to scan in the direction orthogonal to the axial flaw F1 (liftoff in this condition is shown by L in FIG. 1A), so that the detection sensitivity is the highest for the axial flaw F1 among flaws extending in various directions. On the other hand, as shown in FIG. 2B, an amplitude of a differential output at a circumferential flaw F2 occurring in the steel pipe P reaches a maximum when the probe coil 2 is made to scan in the direction orthogonal to the circumferential direction of the steel pipe P (direction of arrow C or D shown in FIG. 2B), and at this time, the detection sensitivity at the circumferential flaw F2 is most improved. However, since the liftoff reaches a maximum when the probe coil 2 is made to scan in the direction orthogonal to the circumferential flaw F2 (liftoff in this condition is L+ΔL as shown in FIG. 1A), the detection sensitivity is the smallest for the circumferential flaw F2 among flaws extending in various directions. And the larger the radius of spinning R of the probe coil 2, the larger the difference in the liftoff is, so that a difference in detection sensitivity between the axial flaw F1 and the circumferential flaw F2 increases. Therefore, for accurately detecting both of the axial flaw F1 and the circumferential flaw F2, and any flaws extending in intermediate directions thereof, it is important to set the radius of spinning R so that the difference in detection sensitivity between the axial flaw F1 and the circumferential flaw F2 falls within an allowable range.

Therefore, the distance R between the spinning center RC of the spinning plate 1 and the center of the probe coil 2 (radius of spinning of the probe coil 2) is set so that the difference between the maximum amplitude of differential output at an axially extending artificial flaw provided in the steel pipe P (maximum amplitude of differential output obtained in the condition shown in FIG. 2A) and the maximum amplitude of differential output at a circumferentially extending artificial flaw provided in the steel pipe P (maximum amplitude of differential output obtained in the condition shown in FIG. 2B) falls within a predetermined allowable range. In this way, since the distance R between the spinning center RC of the probe coil 2 and the center of the probe coil 2 is set so that the difference in detection sensitivity (difference in maximum amplitude of differential output) between an axial flaw (axially extending artificial flaw) and a circumferential flaw (circumferentially extending artificial flaw) in which a difference in detection sensitivity is a maximum falls within a predetermined allowable range, it is possible to make the difference in detection sensitivity fall within the allowable range for any flaws regardless of their extending directions. Therefore, according to the eddy current testing apparatus 100 of the present invention, it is possible to accurately detect any flaws occurring in the steel pipe P regardless of their extending directions with the use of the same probe coil 2.

Liftoff variation in one spin of the probe coil 2 by spinning scanning varies depending on the outer radius of the steel pipe P even when the radius of spinning R of the probe coil 2 is constant (the larger the outer radius of the steel pipe P, the smaller the liftoff variation is). Also even when the liftoff variation is constant, a difference between a maximum amplitude of differential output at an axially extending artificial flaw provided in the steel pipe P and a maximum amplitude of differential output at a circumferentially extending artificial flaw provided in the steel pipe P varies depending on the material of the steel pipe P. Therefore, it is necessary for the radius of spinning R of the probe coil 2 in which the difference in the maximum amplitude of differential output falls within an allowable range to be set in accordance with the outer radius and material of the steel pipe P which is a subject to be tested. Concrete method of setting the radius of spinning R will be described later.

Figure 3A:
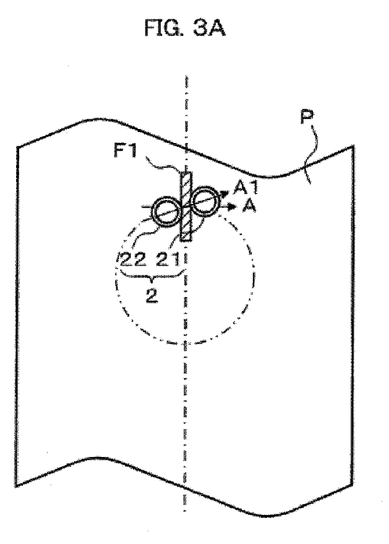
FIG. 3A and FIG. 3B are explanatory views of an alternate example of the probe coil shown in FIGS. 1A and 1B.
Figure 3B:
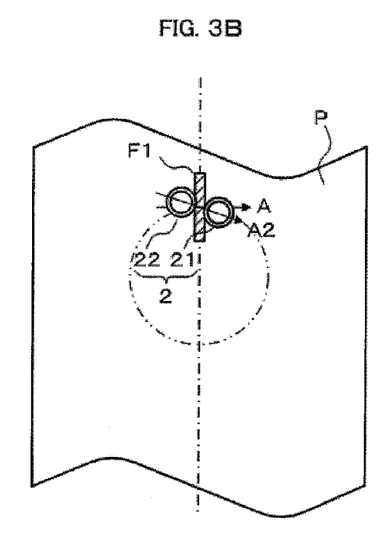

In the present embodiment, the probe coil 2 in which the direction of parallel disposition of the pair of detection coils 21, 22 perfectly coincides with the scanning direction of the probe coil 2 is exemplified, however, the present invention is not limited thereto. In other words, as shown in FIGS. 3A and 3B, the direction of parallel disposition of the pair of detection coils 21, 22 may be inclined from scanning direction (direction of arrow A in the condition shown in FIGS. 3A and 3B) of the probe coil 2 (direction of arrow A1 in FIG. 3A or direction of arrow A2 in FIG. 3B) as far as a differential output is obtained at a flaw (axial flaw F1 in the example shown in FIGS. 3A and 3B) extending in the direction orthogonal to the scanning direction A of the probe coil 2 (differential output is distinguishable from noise signal).

In the present embodiment, the probe coil 2 configured to have the pair of detection coils 21, 22 disposed in parallel with each other along the scanning direction, and to output difference in detection signal between these detection coils 21, 22 (differential output), which is a so-called self comparing type coil is exemplified, however, the present invention is not limited to this. In other words, as a probe coil capable of obtaining differential output about scanning direction of detection signal which corresponds to a detected eddy current induced in a subject to be tested (steel pipe P) in the present invention, a probe coil 2' which is a so-called uniform eddy current coil configured to have a circular excitation coil 23 and a rectangular detection coil 24 (lead wire is wound about the scanning direction) provided in the excitation coil 23 for detecting a magnetic field in the scanning direction of the probe coil (configured to detect magnetic field in the direction of arrow E in the condition shown in FIG. 4) as shown in FIG. 4 may be used.

Figure 4:
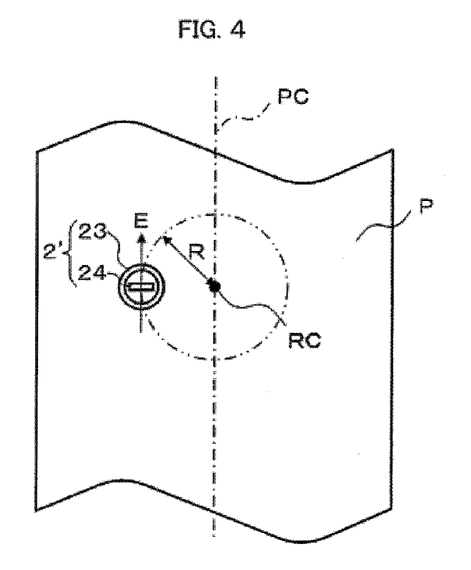
FIG. 4 is a plane view schematically showing other configuration of a probe coil constituting an eddy current testing apparatus according to the present invention.
Figure 5A:
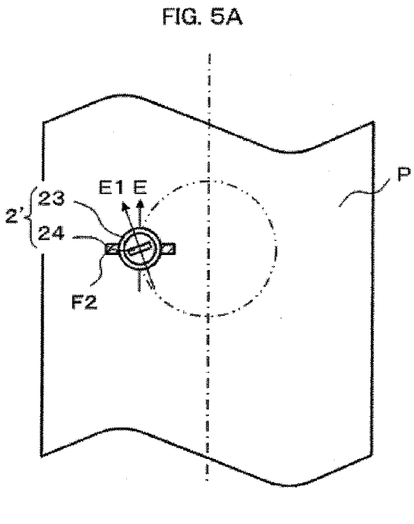
FIGS. 5A and 5B are explanatory views of an alternate example of the probe coil shown in FIG. 4.
Figure 5B:
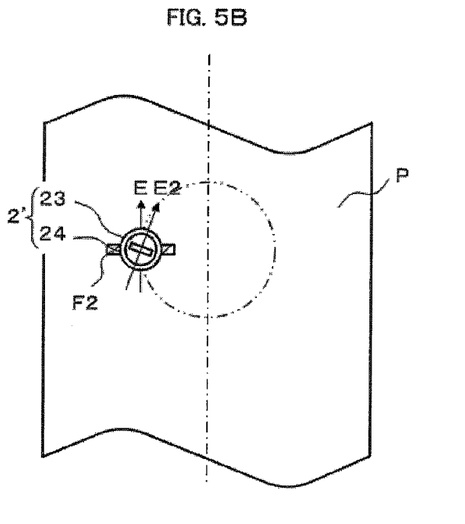

In FIG. 4, the probe coil 2' in which the direction of axial center of the rectangular detection coil 24 perfectly coincides with the scanning direction E of the probe coil 2' is exemplified, however, the present invention is not limited to this. That is, as shown in FIGS. 5A and 5B, the rectangular detection coil 24 may be disposed while the axial center thereof is inclined from the scanning direction E of the probe coil 2' (inclined in the direction of arrow E1 in FIG. 5A or in the direction of arrow E2 in FIG. 5B) as far as differential output is obtained at a flaw (circumferential flaw F2 in the example shown in FIGS. 5A and 5B) extending in the direction orthogonal to the scanning direction E of the probe coil 2' (differential output is distinguishable from noise signal).

In the following, a concrete method of setting a radius of spinning R of the probe coil 2 or 2' will be explained.

Figure 6A:
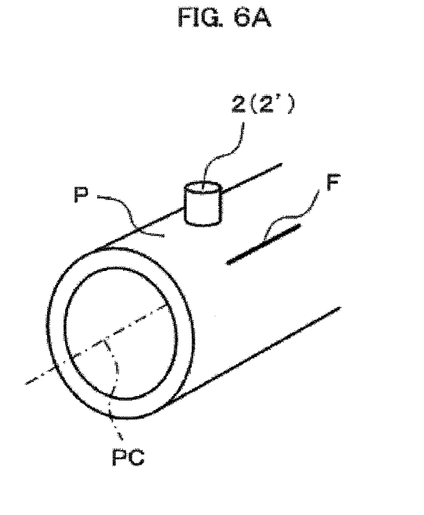
FIG. 6A is a perspective view.
Figure 6B:
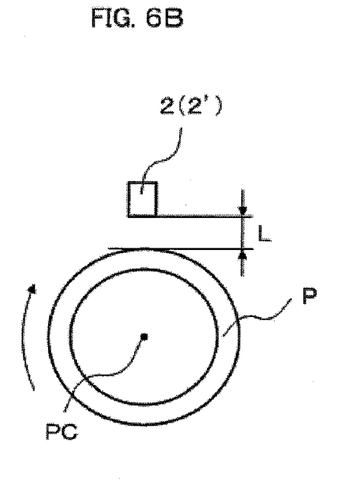
FIG. 6B is a front view.

For setting the radius of spinning R of the probe coil 2 or 2', first, a test for examining influence of liftoff of the probe coil 2 or 2' on the flaw detection sensitivity is conducted using the steel pipe P made of the same material as that of the steel pipe for which flaw testing is to be actually conducted. Concretely, as shown in FIG. 6, axially extending artificial flaw F is provided in the steel pipe P, the probe coil 2 or 2' is disposed at a position which faces with the axial center PC of the steel pipe P and is distant from the steel pipe P by a liftoff L, and a detection sensitivity of the artificial flaw F (maximum amplitude of differential output in artificial flaw F) is evaluated by rotating the steel pipe P in the circumferential direction.

At this time, if the probe coil 2 of self comparing type is used, the direction of parallel disposition of the pair of detection coils 21, 22 is made into coincidence with the direction of parallel disposition in actually testing a flaw by spinning scanning of the probe coil 2. In other words, as shown in FIGS. 2A and 2B as described above, if the direction of parallel disposition of the detection coils 21, 22 is made into perfect coincidence with the scanning direction of the probe coil 2 in an actual flaw testing, the pair of detection coils 21, 22 in the present test are disposed so that the direction of parallel disposition is made into coincidence with the circumferential direction of the steel pipe P because the scanning direction of the probe coil 2 in the present test is circumferential direction of the steel pipe P. Also as shown in FIGS. 3A and 3B as described above, if the direction of parallel disposition of the pair of detection coils 21, 22 is inclined from the scanning direction of the probe coil 2 in an actual flaw testing, the direction of parallel disposition of the pair of detection coils 21, 22 in the present test is inclined in the same manner, from the circumferential direction of the steel pipe P.

Further, if the probe coil 2' which is a so-called uniform eddy current coil is used, the direction of axial center of the rectangular detection coil 24 (magnetic field detecting direction) is made into coincidence with the direction of axial center in actually conducting flaw testing by spinning scanning of the probe coil 2'. That is, as shown in FIG. 4 described before, if the direction of axial center of the rectangular detection coil 24 is made into perfect coincidence with the scanning direction of the probe coil 2' in actual flaw testing, the rectangular detection coil 24 in the present test is disposed so that its direction of axial center is in perfect coincidence with the circumferential direction of the steel pipe P because the scanning direction of the probe coil 2' in the present test is circumferential direction of the steel pipe P. Further, if the axial center of the rectangular detection coil 24 is disposed so that it is inclined from the scanning direction of the probe coil 2' in actual flaw testing as shown in FIGS. 5A and 5B described above, the rectangular detection coil 24 in the present test is also disposed so that its axial center is inclined from the circumferential direction of the steel pipe P.

By repeating the evaluation as explained above while changing the liftoff L between the steel pipe P and the probe coil 2 or 2' within a predetermined range, an influence of the liftoff of the probe coil 2 or 2' on the flaw detection sensitivity is examined.

Figure 7:
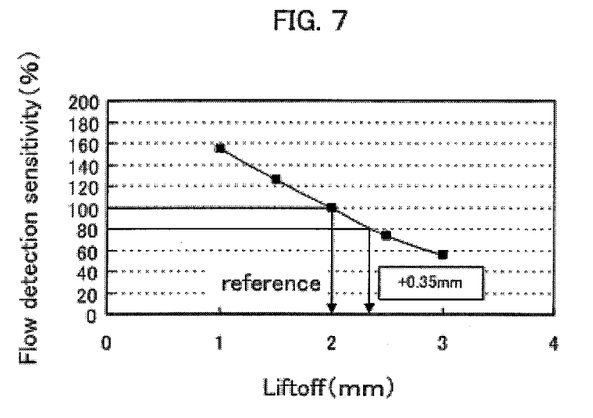
FIG. 7 is a graph showing one example of test result shown in FIG. 6.

FIG. 7 is a graph showing one exemplary result of a test for examining an influence of a liftoff of the self comparing type probe coil 2 on the flaw detection sensitivity in the manner as described above, for a steel pipe P made of low alloy steel (magnetic material). Concretely, the steel pipe P made of low alloy steel and having outer diameter of 140 mm and thickness of 6 mm was provided with 5% notch (0.3 mm deep) extending in the axial direction as an artificial flaw F, and the test was conducted while a liftoff L of the probe coil 2 is changed within the range of 1 mm to 3 mm. The result shown in FIG. 7 demonstrates that when the liftoff L=2 mm is regarded as a reference (flaw detection sensitivity at L=2 mm is 100%), for example, the liftoff in which flaw detection sensitivity decreases by 2 dB (reaches about 80%) compared to the flaw detection sensitivity when liftoff, is set at the reference liftoff is about 2.35 mm. Similar test was conducted also for the probe coil 2' which is a so-called uniform eddy current coil, and similar result as the graph shown in FIG. 7 was obtained.

Therefore, when the allowable range of difference in detection sensitivity between an axial flaw (axially extending artificial flaw) and a circumferential flaw (circumferentially extending artificial flaw) is e.g., 2 dB, (when the detection sensitivity of circumferential flaw is allowed to decrease by up to 2 dB compared to detection sensitivity of axial flaw), the allowable range of liftoff variation in association with spinning scanning of the probe coil 2 or 2' is about 0.35 mm (=2.35 mm−2 mm) in the case shown in FIG. 7. That is, the radius of spinning R of the probe coil 2 or 2' may be set so that ΔL shown in FIG. 1A is equal to or less than 0.35 mm. This radius of spinning R can be geometrically calculated according to the following formula (I) when the outer diameter of the steel pipe P is represented by "2r".

$$R = r \sin[\cos^{-1}\{(r-\Delta L)/r\}] \quad (1)$$

For example, when ΔL=0.35 mm, radius of spinning R to be set for the steel pipe P having an outer diameter of 140 mm (namely, r=70 mm) is about 7 mm according to the above formula (I).

As described above, the radius of spinning R of the probe coil 2 or 2' can be generally set in the following procedure (a) to (c).

(a) Using a steel pipe P made of the same material as that of a steel pipe for which actual flaw testing is to be conducted, influence of liftoff of the probe coil 2 or 2' on flaw detection sensitivity is examined. (In the above example, test result shown in FIG. 7 is obtained.)

(b) Based on the result of examination (a), an allowable range of liftoff variation is calculated (about 0.35 mm in the above example) so that a difference in detection sensitivity falls within a predetermined allowable range of difference in detection sensitivity between an axial flaw and a circumferential flaw (in the above example, 2 dB).

(c) ΔL is set within the allowable range of liftoff variation calculated in the above (b) (in the above example, ΔL=0.35 mm), and the radius of spinning R of the probe coil 2 or 2' is set according to the formula (I) (in the above example, R=7 mm).

As described above, the difference in detection sensitivity between the axial flaw and the circumferential flaw provided in a subject to be tested varies depending on the material of the subject to be tested. In other words, the influence of the liftoff of the probe coil 2 or 2' on the flaw detection sensitivity as shown in FIG. 7 varies depending on the material of the subject to be tested.

Figure 8:
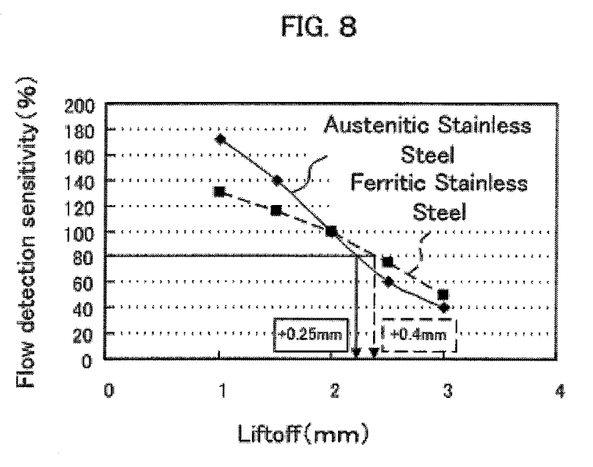
FIG. 8 is a graph showing other example of test result shown in FIG. 6.

FIG. 8 is a graph showing one example of test result in which influence of liftoff of the self comparing type probe coil 2 on the flaw detection sensitivity is examined for each of a steel pipe made of austenitic stainless steel (nonmagnetic material) and a steel pipe made of ferritic stainless steel in the manner as shown in FIG. 7. Concretely, a steel pipe (austenitic stainless steel and ferritic stainless steel) P having an outer diameter of 178 mm and a thickness of 8 mm was provided with 5% notch (0.4 mm deep) extending in the axial direction as an artificial flaw F, and a test was conducted while a liftoff L of the probe coil 2 was changed within the range of 1 mm and 3 mm. Similar test was conducted also for the probe coil 2' which is a so-called uniform eddy current coil, and similar result as the graph shown in FIG. 8 was obtained.

The result shown in FIG. 8 demonstrates that when a liftoff L=2 mm is regarded as a reference (flaw detection sensitivity at L=2 mm is 100%), for example, the liftoff in which flaw detection sensitivity decreases by 2 dB (reaches about 80%) compared to the flaw detection sensitivity when a liftoff is set at the reference liftoff is about 2.25 mm for the case of austenitic stainless steel and about 2.4 mm for the case of ferritic stainless steel. Therefore, an allowable range of liftoff variation in association with spinning scanning of the probe coil 2 or 2' is about 0.25 mm (=2.25 mm−2 mm) for the case of austenitic stainless steel and about 0.4 mm (=2.4 mm−2 mm) for the case of ferritic stainless steel.

As described above, the influence of the liftoff of the probe coil 2 or 2' on the flaw detection sensitivity (allowable range of liftoff variation) varies depending on the material of the subject to be tested. Therefore, it is preferred that the test for examining the influence of the liftoff of the probe coil 2 or 2' is conducted for each material of subject to be tested, and a radius of spinning R of the probe coil 2 or 2' is set for each material of subject to be tested based on the test result.

Table 1 shows one example of a test result of a steel pipe (low alloy steel) provided with an axial flaw (axially extending artificial flaw) and a circumferential flaw (circumferentially extending artificial flaw) by actually conducting spinning scanning of the probe coil 2 or 2' at a radius of spinning R set in the manner as described above.

TABLE 1

| Subject to be tested | Subject to be tested | Steel pipe (outer diameter 140 mm, thickness 6 mm, low alloy steel) | |
|---|---|---|---|
| | Flaw | Axial 5% notch and circumferential 5% notch | |
| Test condition | Probe coil | Self comparing type | Uniform eddy current coil |
| | Test frequency | 100 kHz | |
| | Scanning method | Spinning scanning (500 rpm) of probe coil while steel pipe is kept still | |
| | Radius of spinning (R) | 7 mm | |
| | Reference liftoff (L) | 2 mm | |
| Test result | Flaw detection sensitivity (Relative value) | Axial 5% notch: 100% | Axial 5% notch: 100% |
| | | Circumferential 5% notch: 80% | Circumferential 5% notch: 85% |

As shown in Table 1, even when spinning scanning of the probe coil 2 or 2' was actually conducted, the detection sensitivity for the circumferential flaw (circumferential 5% notch) was 80% or higher, compared to 100% of the detection sensitivity for the axial flaw (axial 5% notch), and was demonstrated to fall within an allowable range (2 dB) of difference in detection sensitivity between predetermined axial flaw and circumferential flaw.

What is claimed is:

1. An eddy current testing method for detecting a flaw occurring in a columnar or cylindrical subject to be tested by conducting spinning scanning of a probe coil disposed to be opposite to the subject to be tested, relative to the subject to be tested, comprising the steps of:

using a probe coil capable of obtaining a differential output about a scanning direction of a detection signal which corresponds to a detected eddy current induced in the subject to be tested as the probe coil;

positioning the probe coil so that a straight line passing a spinning center of the probe coil crosses with an axial center of the subject to be tested at right angles;

preparing a test piece made of the same material as that of the subject to be tested, which is provided with an axially extending artificial flaw and a circumferentially extending artificial flaw whose depth is equivalent to depth of the axially extending artificial flaw, and disposing the test piece opposite to the probe coil;

setting a distance between the spinning center of the probe coil and a center of the probe coil, which is located differently from the spinning center of the probe coil, so that a difference between a maximum amplitude of a differential output at the axially extending artificial flaw provided in the test piece and a maximum amplitude of a differential output at the circumferentially extending artificial flaw provided in the test piece falls within a predetermined range; and conducting spinning scanning of the probe coil relative to the subject to be tested which is not provided with an artificial flaw at the set distance to detect a flaw occurring in the subject to be tested.

2. An eddy current testing apparatus having a spinning plate and a probe coil disposed on the spinning plate and located differently from a spinning center of the spinning plate, for detecting a flaw occurring in a columnar or cylindrical subject to be tested by spinning the spinning plate disposed to be opposite to the subject to be tested, relative to the subject to be tested, thereby conducing spinning scanning of the probe coil, wherein the probe coil is a probe coil capable of obtaining a differential output about a scanning direction of a detection signal which corresponds to a detected eddy current induced in the subject to be tested, the spinning plate is positioned so that a straight line passing the spinning center of the spinning plate crosses with an axial center of the subject to be tested at right angles, relative to a test piece made of the same material as that of the subject to be tested, which is provided with an axially extending artificial flaw and a circumferentially extending artificial flaw whose depth is equivalent to depth of the axially extending artificial flaw, a distance between the spinning center of the spinning plate and a center of the probe coil is set so that a difference between a maximum amplitude of a differential output at the axially extending artificial flaw provided in the test piece and a maximum amplitude of a differential output at the circumferentially extending artificial flaw provided in the test piece falls within a predetermined range, and spinning scanning of the probe coil is conducted relative to the subject to be tested which is not provided with an artificial flaw by spinning the spinning plate to detect a flaw occurring in the subject to be tested.

* * * * *

UNITED STATES PATENT AND TRADEMARK OFFICE
CERTIFICATE OF CORRECTION

PATENT NO. : 8,552,717 B2  Page 1 of 1
APPLICATION NO. : 12/531840
DATED : October 8, 2013
INVENTOR(S) : Hyodo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 809 days.

Signed and Sealed this
Fifteenth Day of September, 2015

Michelle K. Lee
*Director of the United States Patent and Trademark Office*